United States Patent
Lin et al.

(10) Patent No.: US 11,340,662 B2
(45) Date of Patent: May 24, 2022

(54) PORTABLE ELECTRONIC DEVICE AND DISINFECTING AND STERILIZING METHOD THEREOF

(71) Applicants: Yi-Chun Lin, Taipei (TW); Ya-Hui Tseng, Taipei (TW); I-Kai Liu, Taipei (TW); Po-Ching Chiang, Taipei (TW); Chien-Lun Sun, Taipei (TW); Yen-Kang Chen, Taipei (TW); Jih-Houng Lee, Taipei (TW); Chih-Chien Liu, Taipei (TW)

(72) Inventors: Yi-Chun Lin, Taipei (TW); Ya-Hui Tseng, Taipei (TW); I-Kai Liu, Taipei (TW); Po-Ching Chiang, Taipei (TW); Chien-Lun Sun, Taipei (TW); Yen-Kang Chen, Taipei (TW); Jih-Houng Lee, Taipei (TW); Chih-Chien Liu, Taipei (TW)

(73) Assignee: COMPAL ELECTRONICS, INC., Taipei (TW)

( * ) Notice: Subject to any disclaimer, the term of this patent is extended or adjusted under 35 U.S.C. 154(b) by 0 days.

(21) Appl. No.: 17/192,891

(22) Filed: Mar. 5, 2021

(65) Prior Publication Data
US 2021/0286412 A1  Sep. 16, 2021

Related U.S. Application Data

(60) Provisional application No. 62/987,362, filed on Mar. 10, 2020, provisional application No. 63/023,870, filed on May 13, 2020.

(51) Int. Cl.
G06F 1/16     (2006.01)
A61L 2/00     (2006.01)

(52) U.S. Cl.
CPC .......... *G06F 1/1681* (2013.01); *A61L 2/0047* (2013.01); *G06F 1/1677* (2013.01); *G06F 1/1679* (2013.01); *A61L 2202/14* (2013.01)

(58) Field of Classification Search
CPC ............................ G06F 1/1677; G06F 1/1681
See application file for complete search history.

(56) References Cited

U.S. PATENT DOCUMENTS 6,040,822 A * 3/2000 Decker .................. H01H 13/70
345/172
6,161,944 A * 12/2000 Leman .................. G06F 3/0202
362/802

(Continued)

FOREIGN PATENT DOCUMENTS

CN        2594420      12/2003
CN      201223570       4/2009

(Continued)

*Primary Examiner* — Adrian S Wilson
(74) *Attorney, Agent, or Firm* — JCIPRNET

(57) ABSTRACT

A portable electronic device including a first body, a second body, a hinge mechanism, a control unit, a sensor unit, a sterilization module, and a shielding module, is provided. The first body has a first inner surface. The second body has a second inner surface. The hinge mechanism is connected between the first body and the second body. The control unit is disposed in the first body or the second body. The sensor unit is disposed in the first body or the second body and coupled to the control unit. The sterilization module is disposed at the hinge mechanism and coupled to the control unit, the sterilization module is configured to generate light for sterilization and disinfection. The shielding module is disposed on the hinge mechanism and the shielding module can move relative to the hinge mechanism.

27 Claims, 9 Drawing Sheets

(56) References Cited

U.S. PATENT DOCUMENTS

| | | | |
|---|---|---|---|
| 6,380,921 B2* | 4/2002 | Nakamura | G06F 1/1626 |
| | | | 345/87 |
| 6,567,137 B1* | 5/2003 | Moon | G02B 6/0043 |
| | | | 349/63 |
| 7,686,466 B2* | 3/2010 | Lev | G06F 1/1684 |
| | | | 362/269 |
| 8,009,424 B2 | 8/2011 | Zhu et al. | |
| 8,926,111 B2* | 1/2015 | Weng | F21V 33/0052 |
| | | | 362/85 |
| 9,195,275 B2* | 11/2015 | Liu | G06F 1/1684 |
| 2002/0085371 A1* | 7/2002 | Katayama | G06F 1/1637 |
| | | | 362/23.05 |
| 2004/0062033 A1* | 4/2004 | Chu-Chia | G06F 1/1637 |
| | | | 362/84 |
| 2007/0253182 A1* | 11/2007 | Motai | G06F 1/1684 |
| | | | 362/23.03 |
| 2011/0007492 A1* | 1/2011 | Sauer | G06F 1/1643 |
| | | | 362/85 |
| 2011/0117968 A1* | 5/2011 | Eromaki | G06F 3/04886 |
| | | | 345/173 |

FOREIGN PATENT DOCUMENTS

| | | |
|---|---|---|
| CN | 203386195 | 1/2014 |
| CN | 107704029 | 2/2018 |
| CN | 110032249 | 7/2019 |
| CN | 110703860 | 1/2020 |
| TW | I354878 | 12/2011 |

* cited by examiner

PORTABLE ELECTRONIC DEVICE AND DISINFECTING AND STERILIZING METHOD THEREOF

CROSS-REFERENCE TO RELATED APPLICATION

This application claims the priority benefits of U.S. provisional application Ser. No. 62/987,362, filed on Mar. 10, 2020 and U.S. provisional application Ser. No. 63/023,870, filed on May 13, 2020. The entirety of each of the above-mentioned patent applications is hereby incorporated by reference herein and made a part of this specification.

BACKGROUND

Technical Field

This disclosure relates to an electronic device, and in particular to a portable electronic device with sterilization and disinfection functions.

Description of Related Art

Portable electronic devices include a laptop, a tablet computer, or a smart phone. As the hands often touch the keyboard and the screen of the portable electronic devices, it is easy for these two areas to accumulate dirt and breed harmful substances such as bacteria and viruses. An existing cleaning means is to use a piece of woven cloth or paper combined with disinfectant to wipe and decontaminate the keyboard and the surface of the screen. However, the residual disinfectant may damage the surface of the electronic device, and there is also a risk of the disinfectant leaking and causing damage to the electronic device. Also, the disinfectant after evaporation is easy to be inhaled into the human lungs, which may have health concerns.

In addition, the existing portable electronic devices require preparation of their own woven cloth, paper, and disinfectant, and rely on manual wiping. This causes inconvenience in cleaning when the portable electronic device is being carried outside.

SUMMARY

This disclosure provides a portable electronic device with automatic sterilization and disinfection functions, so as to replace an existing cleaning means of manual wiping.

A portable electronic device of the disclosure includes a first body, a second body, a hinge mechanism, a control unit, a sensor unit, a sterilization module, and a shielding module. The first body has a first inner surface. The second body has a second inner surface. The hinge mechanism is connected between the second body and the first body. The control unit is disposed in the first body or the second body. The sensor unit is disposed in the first body or the second body and coupled to the control unit. The sterilization module is disposed in the hinge mechanism and coupled to the control unit. The sterilization module is suitable for generating at least one light for sterilization and disinfection. The shielding module has at least one light-passable opening. The shielding module is disposed on the hinge mechanism and can move relative to the hinge mechanism. The shielding module is coupled to the control unit.

The control unit is suitable for activating the sterilization module and driving the shielding module to move to a first position, the at least one light-passable opening is opposite to the sterilization module, and the light for sterilization and disinfection is suitable for passing through multiple light-passable openings when the sensor unit detects that the first body and the second body are closed relative to each other. The control unit is suitable for shutting down the sterilization module and driving the shielding module to move to a second position to block at least one optical path of the sterilization module when the sensor unit detects that the first body and the second body are unfolded relative to each other.

The disinfecting and sterilizing method of the disclosure is suitable for a portable electronic device having a first body, a second body, a hinge mechanism, a control unit, a sensor unit, a sterilization module and a shielding module. The hinge mechanism is connected between the second body and the first body. The control unit is disposed in the first body or the second body. The sensor unit is disposed in the first body or the second body and coupled to the control unit. The sterilization module is disposed in the hinge mechanism and coupled to the control unit. The shielding module is disposed on the hinge mechanism and can move relative to the hinge mechanism. The shielding module is coupled to the control unit. The disinfecting and sterilizing method includes the following steps. The sensor unit detects that the first body and the second body are closed relative to each other. The control unit activates the sterilization module and generates at least one light for sterilization and disinfection. The control unit drives the shielding module to move to a first position, enabling at least one optical path of the sterilization module to pass through at least one light-passable opening of the shielding module. And, the control unit shuts down the sterilization module and drives the shielding module to move to a second position, so as to block at the least one optical path of the sterilization module.

In an embodiment of the disclosure, the shielding module is slidably disposed on the hinge mechanism, and is suitable for switching between the first position and the second position.

In an embodiment of the disclosure, a lock is further included, which is coupled to the control unit and includes a lower latch and an upper latch. The lower latch is disposed at the first body and the upper latch is disposed at the second body. The control unit controls the lower latch and the upper latch to be locked to each other when the two bodies are closed relative to each other.

In an embodiment of the disclosure, the control unit shuts down the sterilization module and drives the shielding module to move to the second position when the lock is unlocked by an external force.

In an embodiment of the disclosure, the sterilization module includes multiple ultra-violet (UV) light sources, and the light for sterilization and disinfection is a UV light.

In an embodiment of the disclosure, each of the lights for sterilization and disinfection is suitable for reflection and transmission between the first inner surface and the second inner surface.

In an embodiment of the disclosure, a timer is further included, which is disposed in the first body or the second body and coupled to the control unit. The timer sets a preset time when the first body and the second body are closed relative to each other. The control unit shuts down the sterilization module and drives the shielding module to move to the second position after countdown of the preset time is completed.

In an embodiment of the disclosure, at least one safety switch is further included, which is disposed at two sides of the second body away from the hinge mechanism and coupled to the control unit. The control unit shuts down the sterilization module and drives the shielding module to move to the second position when the at least one safety switch is pressed by an external force.

In an embodiment of the disclosure, an indicator element that is coupled to the control unit is further included. The control unit transmits a locked signal to the indicator element and a first indicator light is displayed when the lower latch and the upper latch are locked to each other. The control unit transmits an unlocked signal to the indicator element and a second indicator light is displayed when the lower latch and the upper latch are unlocked from each other.

In an embodiment of the disclosure, an indicator element that is coupled to the sterilization module is further included. The indicator element displays a first indicator light when the sterilization module is switched on, and the indicator element displays a second indicator light when the sterilization module is shut down.

In an embodiment of the disclosure, an indicator element that is coupled to the shielding module is further included. The indicator element displays a first indicator light when the shielding module moves to the first position. The indicator element displays a second indicator light when the shielding module moves to the second position.

In an embodiment of the disclosure, the sensor unit includes a Hall sensor and a magnetic part. The Hall sensor is disposed in the first body and coupled to the control unit. The magnetic part is disposed in the second body and is opposite to the Hall sensor. The Hall sensor senses a change in a magnetic field of the magnetic part, so as to convert the change into an included angle between the first body and the second body.

In an embodiment of the disclosure, the sensor unit includes a gravity sensor, which is disposed in the second body and coupled to the control unit.

In an embodiment of the disclosure, multiple light-guiding elements are further included, which are disposed in the first body. Each of the light-guiding elements has a light-incident portion, a guiding portion, and a light-emitting portion. Each of the light-incident portions corresponds to each of the UV light sources, each of the guiding portions is distributed on the first inner surface, and each of the light-emitting portions is away from the shielding module.

In an embodiment of the disclosure, each of the light-guiding elements may be a light-guiding plate, a light-guiding rod, or an optical fiber.

In an embodiment of the disclosure, a reflective layer is further included, which is disposed at the first inner surface or the second inner surface corresponding to the first body and the second body.

In an embodiment of the disclosure, a first light barrier plate and a second light barrier plate are further included. The first light barrier plate is disposed around a first outer edge of the first body, and the second light barrier plate is disposed around a second outer edge of the second body. The first light barrier plate and the second light barrier plate are tightly fitted to each other when the first body and the second body are closed relative to each other, so as to seal a gap between the first body and the second body.

In an embodiment of the disclosure, an end of the first light barrier plate covers the gap and is tightly fitted to an end of the second light barrier plate.

In an embodiment of the disclosure, an end of the second light barrier plate covers the gap and is tightly fitted to an end of the first light barrier plate.

Based on the above, the portable electronic device of the disclosure includes the sterilization module, the control unit, and the sensor unit. The control unit activates the sterilization module and generates the light for sterilization and disinfection when the sensor unit detects that the first body and the second body are closed relative to each other, so as to irradiate the first inner surface of the first body and the second inner surface of the second body to achieve sterilization and disinfection. The control unit shuts down the sterilization module and uses the shielding module to block the sterilization module as a protective measure when the sensor unit detects that the first body and the second body are unfolded relative to each other, so as to prevent the leakage of the light for sterilization and disinfection from causing damage to the human body.

Furthermore, the portable electronic device automatically undergoes or shuts down the sterilization and disinfection procedure by determining whether it is in the closed state or the unfolded state, thereby replacing the existing cleaning means of manual wiping.

To make the aforementioned more comprehensible, several embodiments accompanied by drawings are described in detail as follows.

DESCRIPTION OF THE EMBODIMENTS

Figure 1A:
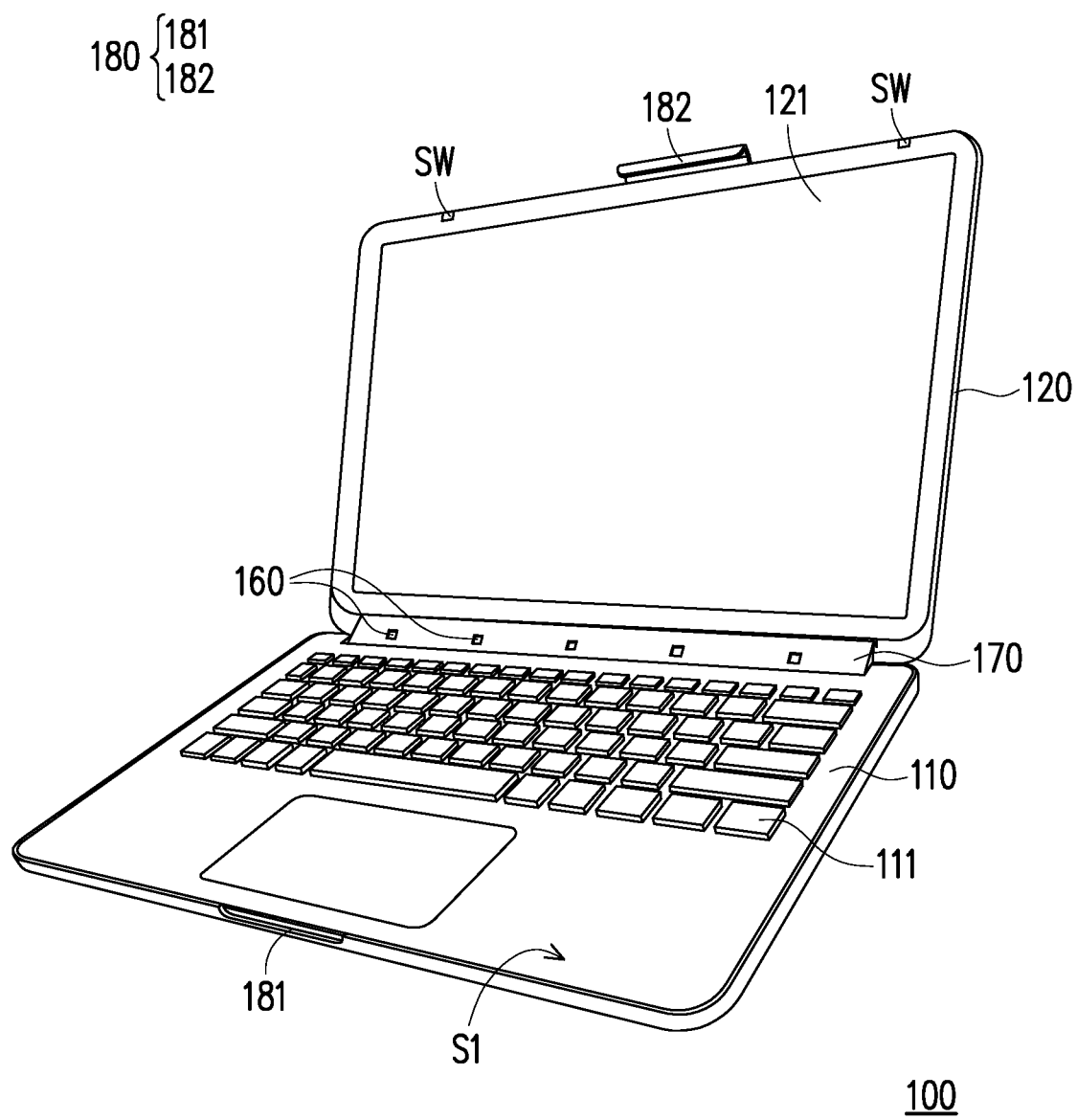
FIG. 1A is a three-dimensional schematic view of a portable electronic device according to an embodiment of the disclosure when it is unfolded to more than 90 degrees.
Figure 1B:
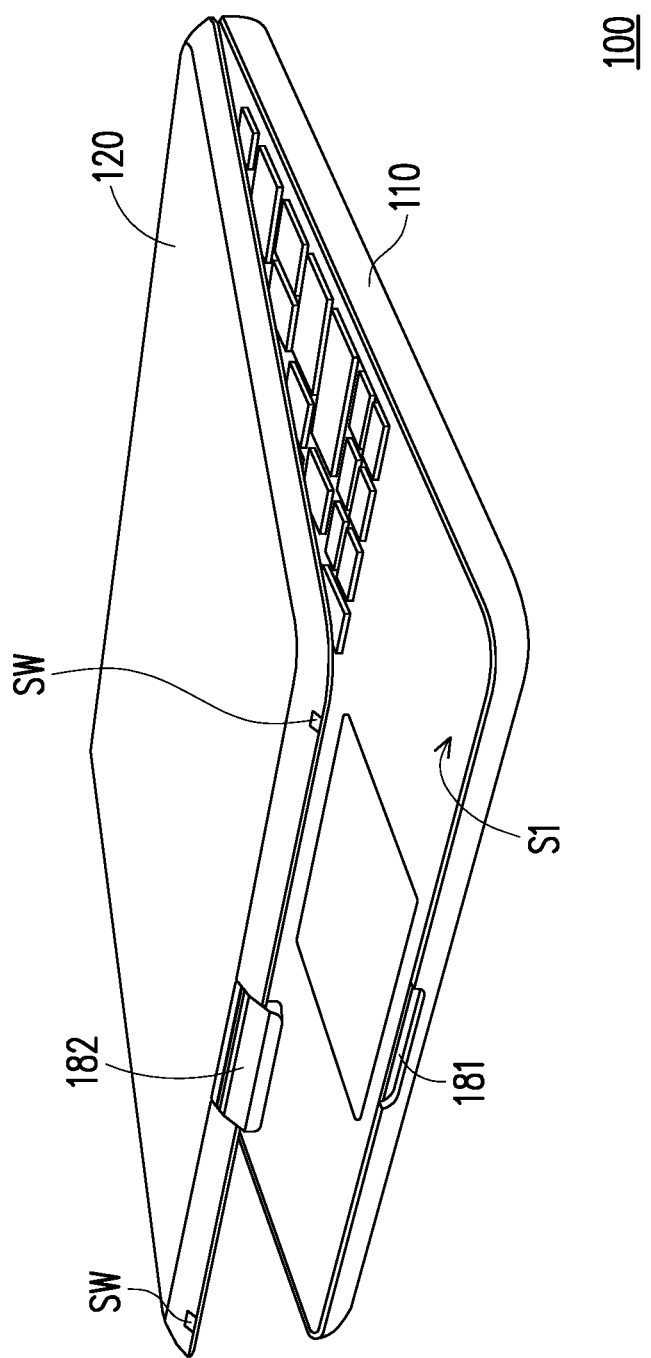
FIG. 1B is a three-dimensional schematic view of the portable electronic device in FIG. 1A when it is unfolded to less than 90 degrees.
Figure 1C:
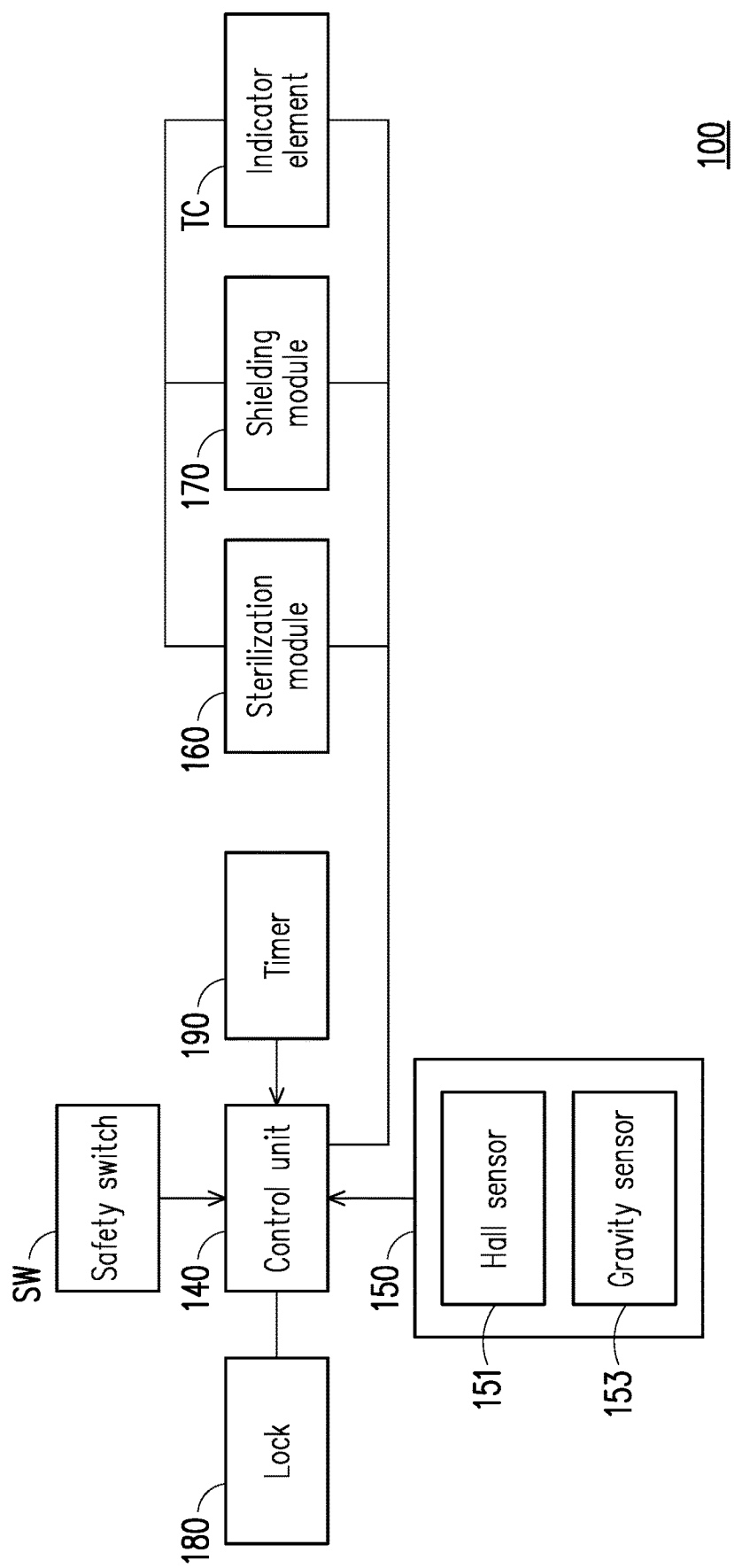
FIG. 1C is a schematic circuit block view of the portable electronic device in FIG. 1A.
Figure 1D:
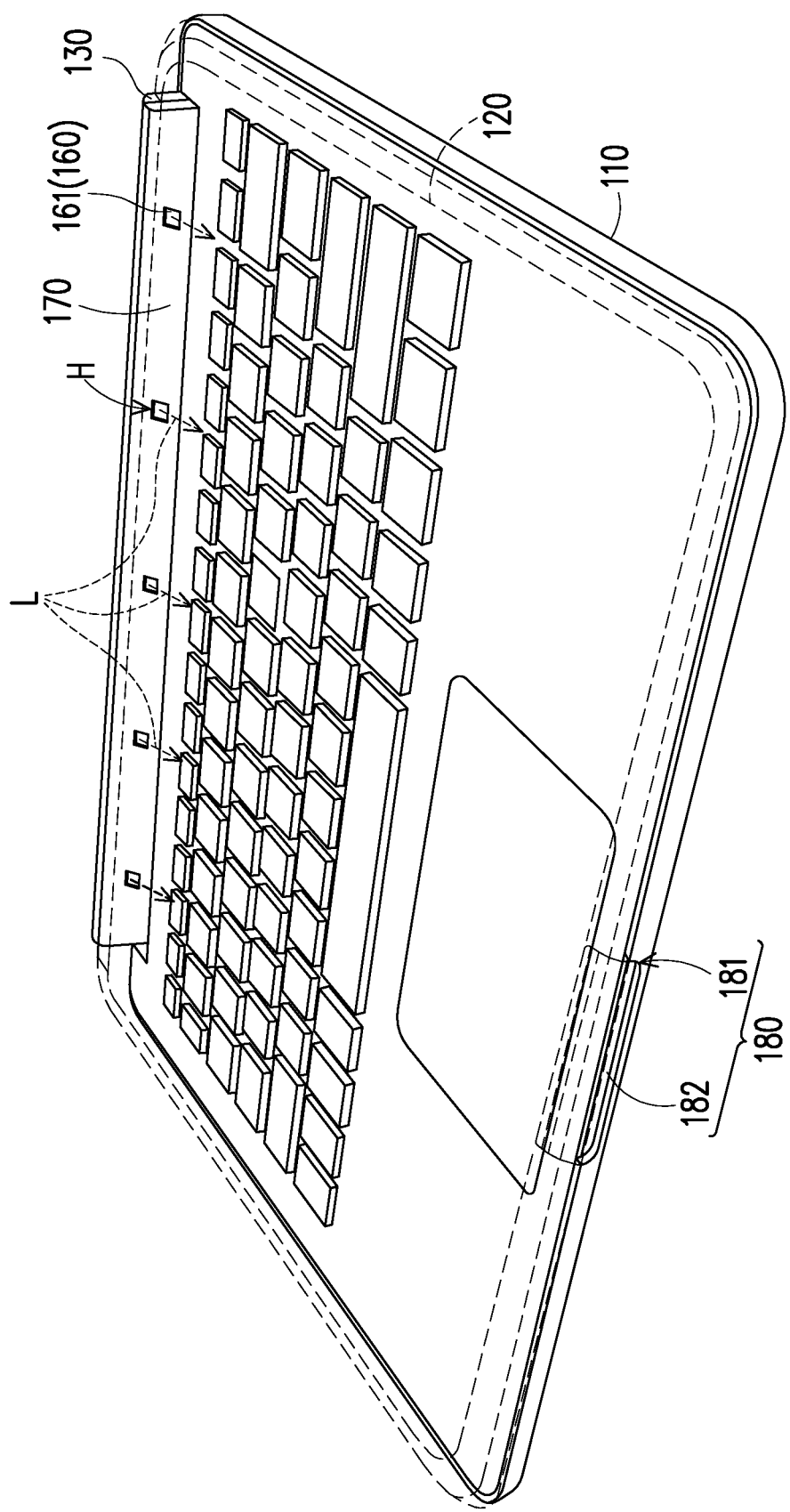
FIG. 1D is a three-dimensional schematic view of the portable electronic device in FIG. 1A in a closed state.

FIG. 1A is a three-dimensional schematic view of a portable electronic device according to an embodiment of the disclosure when it is unfolded to more than 90 degrees. FIG. 1B is a three-dimensional schematic view of the portable electronic device in FIG. 1A when it is unfolded to less than 90 degrees. FIG. 1C is a schematic circuit block view of the portable electronic device in FIG. 1A. FIG. 1D is a three-dimensional schematic view of the portable electronic device in FIG. 1A in a closed state.

With reference to FIGS. 1A to 1C, a portable electronic device 100 of the embodiment takes a notebook computer as an example. In other embodiments, a tablet computer, a smart phone or other similar electronic equipment may also be used.

The portable electronic device 100 includes a first body 110, a second body 120, a hinge mechanism 130, a control unit 140, a sensor unit 150, a sterilization module 160, and a shielding module 170.

The first body 110 is, for example, a logic body that has a first inner surface S1 and a keyboard 111. The first body 110 is configured to accommodate electronic components such as a motherboard, a central processing unit, a graphics card, and a storage hard disk. The second body 120 is, for example, a display body that has a second inner surface S2 and a display panel 121. The second body 120 is configured to output an image. The hinge mechanism 130 is connected between the first body 110 and the second body 120, therefore the first body 110 and the second body 120 are suitable for unfolding or closing relative to each other. The control unit 140 is disposed in the first body 110 or the second body 120 to serve as a control core. The sensor unit 150 is disposed in the first body 110 or the second body 120 and coupled to the control unit 140. The sensor unit 150 is configured to detect an unfolded state and a closed state of the first body 110 and the second body 120. The sterilization module 160 is disposed in the hinge mechanism 130 and coupled to the control unit 140, and is suitable for generating at least one light L for sterilization and disinfection and irradiating the first inner surface S1 or the second inner surface S2 through an at least one optical path P. The shielding module 170 has at least one light-passable opening H. The shielding module 170 is disposed on the hinge mechanism 130 and may move relative to the hinge mechanism 130. The shielding module 170 is coupled to the control unit 140.

In the embodiment, the shielding module 170 may slide relative to the hinge mechanism 130, enabling the shielding module 170 to switch between a first position N1 and a second position N2.

Figure 2A:
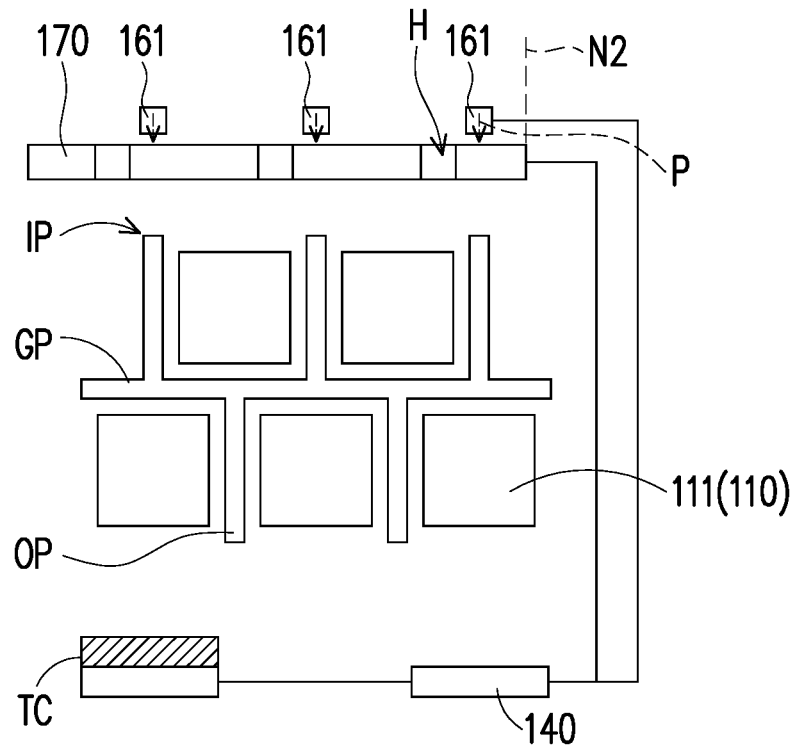
FIG. 2A is a schematic plan view of the portable electronic device in FIG. 1A or FIG. 1B that has not undergone a sterilization and disinfection procedure.
Figure 2B:
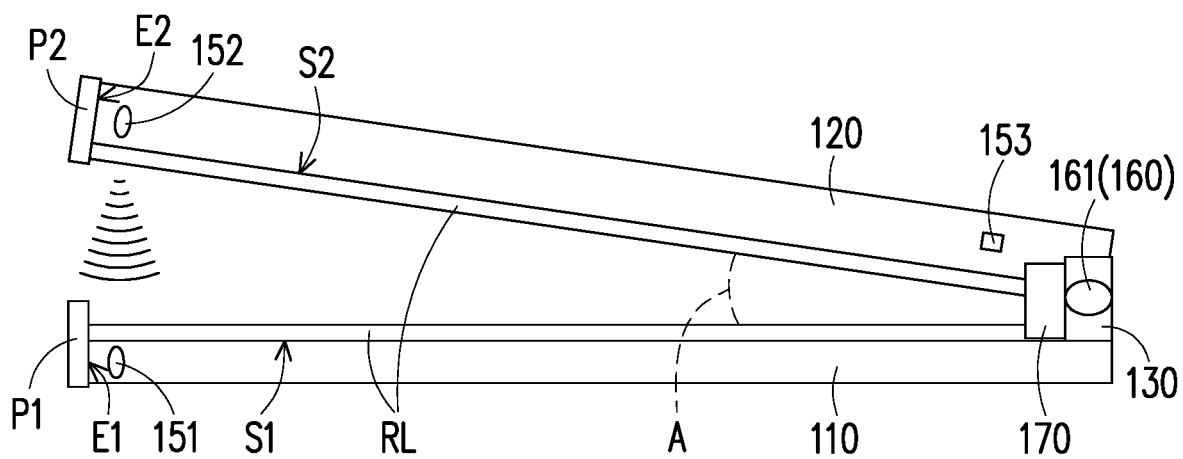
FIG. 2B is a schematic side plan view of the portable electronic device in FIG. 2A in an unfolded state.
Figure 2C:
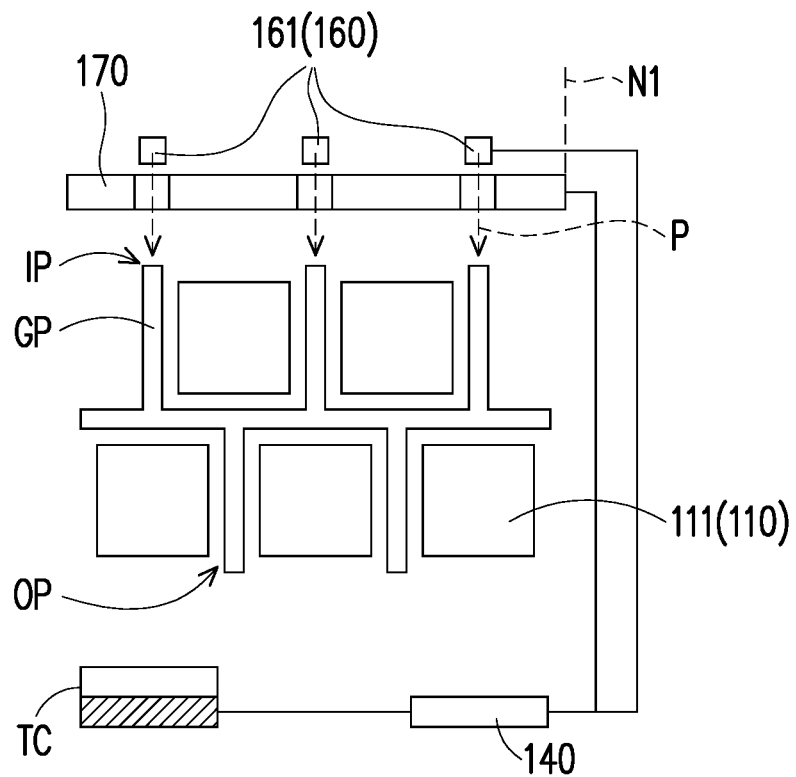
FIG. 2C is a schematic plan view of the portable electronic device in FIG. 1C undergoing the sterilization and disinfection procedure.
Figure 2D:
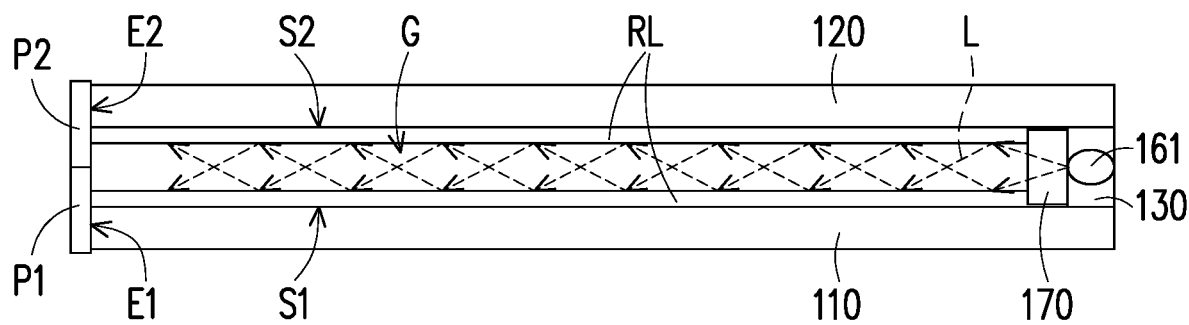
FIG. 2D is a schematic side plan view of the portable electronic device in FIG. 2C in the closed state.

FIG. 2A is a schematic plan view of the portable electronic device in FIG. 1A or FIG. 1B that has not undergone a sterilization and disinfection procedure. FIG. 2B is a schematic side plan view of the portable electronic device in FIG. 2A in the unfolded state. FIG. 2C is a schematic plan view of the portable electronic device in FIG. 1C undergoing the sterilization and disinfection procedure. FIG. 2D is a schematic side plan view of the portable electronic device in FIG. 2C in the closed state.

With reference to FIGS. 1C, 1D, 2C and 2D, the sensor unit 150 transmits a closed signal to the control unit 140 when it detects that the first body 110 and the second body 120 are closed relative to each other. The control unit 140 is suitable for activating the sterilization module 160 and driving the shielding module 170 to move to the first position N1 after interpreting the closed signal, enabling multiple of the light-passable opening H of the shielding module 170 to be opposite to the sterilization module 160 and multiple optical paths P of the light L for sterilization and disinfection are suitable for passing through the multiple light-passable openings H and irradiating the first inner surface S1, the keyboard 111, the second inner surface S2 and the display panel 121. In short, the portable electronic device 100 of the disclosure detects a current state of usage according to the sensor unit 150, and then the control unit 140 controls the sterilization module 160 to perform a sterilization and disinfection procedure on the first body 110 and the second body 120.

With reference to FIGS. 1A, 1B, 1C, 2A and 2B, the sensor unit 150 transmits an unfolded signal to the control unit 140 when it detects that the first body 110 and the second body 120 are unfolded relative to each other. The control unit 140 interprets the unfolded signal, and then shuts down the sterilization module 160 and drives the shielding module 170 to move to the second position N2, so as to block at least one of the optical paths P of the sterilization module 160 to achieve double protection.

Furthermore, with reference to FIGS. 1C, 2B and 2D, the sensor unit 150 of the embodiment includes a Hall sensor 151, a magnetic part 152, and a gravity sensor 153.

The Hall sensor 151 is disposed in the first body 110 and coupled to the control unit 140. The magnetic part 152 is disposed in the second body 120 and is opposite to the Hall sensor 151. The Hall sensor 151 is suitable for sensing a change in a magnetic field of the magnetic part 152, so as to convert the change into an included angle A between the first body 110 and the second body 120 when the first body 110 and the second body 120 move relative to each other. The first body 110 and the second body 120 are closed relative to each other when the included angle A is equal to zero degrees (refer to FIG. 2D). The first body 110 and the second body 120 are unfolded relative to each other when the included angle A is greater than zero degrees (refer to FIG. 2B). The gravity sensor 153 is disposed in the second body 120 and coupled to the control unit 140, and is configured to sense shaking of the first body 110 or the second body 120.

With reference to FIGS. 1C, 1D and 2A, the sterilization module 160 of the embodiment includes multiple ultraviolet (UV) light sources 161. The multiple UV light sources 161 are disposed on the hinge mechanism 130 and correspond to the multiple light-passable openings H of the shielding module 170. Each of the UV light sources 161 is suitable for generating the light L for sterilization and disinfection. Each of the optical paths P of each of the lights L for sterilization and disinfection is suitable for passing through the corresponding light-passable opening H when the shielding module 170 moves to the first position N1. Therefore, the multiple lights L for sterilization and disinfection are suitable for reflecting and transmitting between the first inner surface S1 and the second inner surface S2, thereby irradiating the first inner surface S1, the keyboard 111, the second inner surface S2 and the display panel 121.

In other embodiments, the multiple UV light sources may also be disposed on an edge of the hinge mechanism, a rear edge or a front palm rest region of the first inner surface of the first body, and an outer edge of the second inner surface of the second body. The disclosure does not limit installation position of the multiple UV light sources.

With reference to FIGS. 1A to 1D, the portable electronic device 100 further includes a lock 180, which is coupled to the control unit 140 and includes a lower latch 181 and an upper latch 182. The lower latch 181 is disposed at the first body 110, and the upper latch 182 is disposed at the second body 120. The control unit 140 controls the lower latch 181 and the upper latch 182 to be locked to each other when the first body 110 and the second body 120 are closed relative to each other, so as to prevent the first body 110 and the second body 120 from unfolding from each other due to collision with an external force.

With reference to FIGS. 2A and 2B, the control unit 140 receives the unlocked signal, and synchronously shuts down the sterilization module 160 and drives the shielding module 170 to block the sterilization module 160 when the lock 180 is unlocked by an external force (such as manual unlocking or collision due to an external force).

With reference to FIGS. 1C and 1D, the portable electronic device 100 further includes a timer 190, which is disposed at the first body 110 or the second body 120 and coupled to the control unit 140. The timer 190 sets a preset time when the first body 110 and the second body 120 are closed relative to each other and transmits a completion signal to the control unit 140 after countdown of the preset time is completed. Then, the control unit 140 shuts down the sterilization module 160 and drives the shielding module 170 to move to the second position N2 to block the multiple optical paths P of the sterilization module 160 (refer to FIG. 2A). Furthermore, the user may set a length of the preset time through a built-in software, thereby setting irradiation duration of the sterilization module 160.

With reference to FIGS. 1B, 1C and 2A, the portable electronic device 100 further includes multiple safety switches SW, which are disposed at two sides of the second body 120 away from the hinge mechanism 130 and coupled to the control unit 140. An abnormal signal is transmitted to the control unit 140 when each of the safety switches SW is pressed by an external force. Then, the control unit 140 shuts down the sterilization module 160 and drives the shielding module 170 to block the sterilization module 160. Furthermore, the safety switches SW are located on two sides of the second body 120, and is configured to detect the closed state of the second body 120 and the first body 110, so as to prevent a scenario whereby the light L for sterilization and disinfection is leaked due to displacement of the second body 120 by an external force.

With reference to FIGS. 1B, 1C, 2A and 2C, the portable electronic device 100 further includes an indicator element TC, which is disposed at the first body 110 and coupled to the control unit 140. With reference to FIGS. 1D and 2C, the control unit 140 transmits a locked signal to the indicator element TC and a first indicator light (such as a red indicator light) is displayed when the lower latch 181 and the upper latch 182 are locked to each other, so as to remind a user that the sterilization and disinfection procedure is currently in progress. With reference to FIGS. 1D and 2A, the control unit 140 transmits an unlocked signal to the indicator element TC and a second indicator light (such as a green indicator light) is displayed when the lower latch 181 is unlocked from the upper latch 182, so as to remind the user that the sterilization and disinfection procedure has been completed.

With reference to FIG. 1D, in the embodiment, the indicator element TC is coupled to the sterilization module 160. The indicator element TC displays the first indicator light (such as a red indicator light) when the sterilization module 160 is switched on, so as to remind the user that the sterilization and disinfection procedure is currently in progress. The indicator element TC displays the second indicator light (such as a green indicator light) when the sterilization module 160 is shut down, so as to remind the user that the disinfection and sterilization procedure has been completed.

With reference to FIG. 1D, in the embodiment, the indicator element TC is coupled to the shielding module 170. With reference to FIG. 2C, the indicator element TC displays the first indicator light (such as a red indicator light) when the multiple light-passable openings H of the shielding module 170 are opposite to the sterilization module 160, so as to remind the user that the disinfection and sterilization procedure is currently in progress. With reference to FIG. 2A, the indicator element TC displays the second indicator light (such as a green indicator light) when the shielding module 170 blocks the sterilization module 160, so as to remind the user that the disinfection and sterilization procedure has been completed.

With reference to FIG. 2C, multiple light-guiding elements LG are included, which are disposed at the first inner surface S1 of the first body 110. Each of the light-guiding elements LG has a light-incident portion IP, a guiding portion GP, and a light-emitting portion OP. Each of the light-incident portions IP corresponds to each of the UV light sources 161, each of the guiding portions GP is distributed on the first inner surface S1, and each of the light-emitting portion OP is away from the shielding module 170. In detail, the light-guiding element LG and the light-emitting portion OP are suitable for transmitting the light L for sterilization and disinfection generated by each of the UV light sources 161 to in-between the first body 110 and the second body 120 through the principle of scattering, so as to implement uniform irradiation. In the embodiment, each of the light-guiding elements LG may be a light-guiding plate, a light-guiding rod, or an optical fiber.

With reference to FIG. 2D, the portable electronic device 100 further includes a reflective layer RL, which is disposed on the first inner surface S1 and/or the second inner surface S2 corresponding to the first body 110 and the second body 120, and is configured to enhance reflection efficiency of the light L for sterilization and disinfection (UV light) between the first inner surface S1 and the second inner surface S2.

In detail, in the embodiment, the reflective layer RL is, for example, a Teflon transparent film, which is sprayed on the first inner surface S1 of the first body 110 and the second inner surface S2 of the second body 120, and attached to the keyboard 111 and the display panel 121, so as to improve smoothness of the surfaces of the first body 110 and the second body 120 and a reflection coefficient. Energy attenuation may be reduced to increase a reflection distance of the light L for sterilization and disinfection (UV light) when the light L for sterilization and disinfection (UV light) is transmitted between the first body 110 and the second body 120. In other embodiments, a Teflon material may be added to manufacturing materials of the first body and the second body to fill pores in the manufacturing materials, thereby improving smoothness of the materials of the first body and the second body.

Figure 3A:
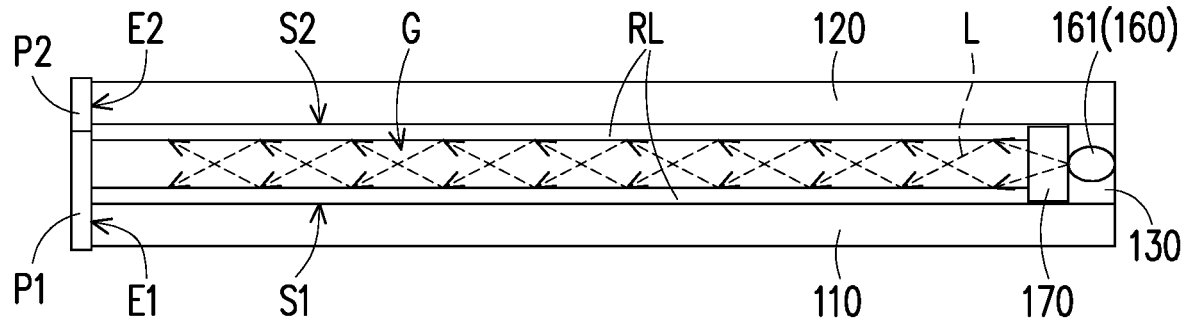
FIG. 3A is a schematic plan view of the portable electronic device of FIG. 1C combined with a first light barrier plate and a second light barrier plate of an embodiment.
Figure 3B:
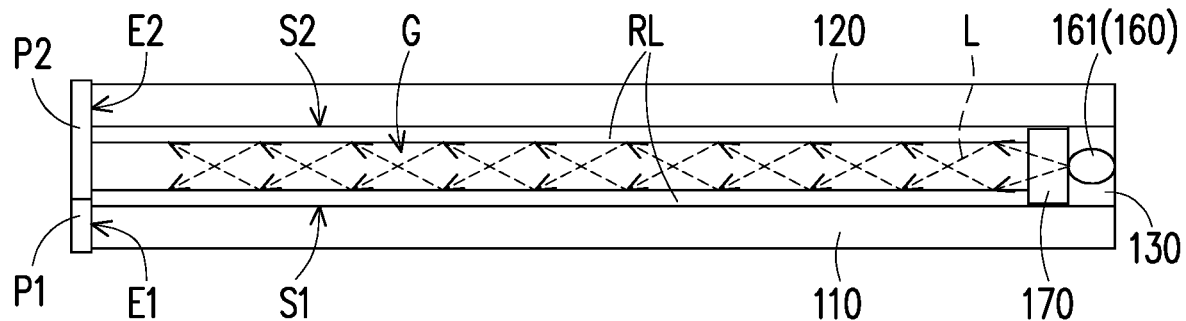
FIG. 3B is a schematic plan view of the portable electronic device of FIG. 2A combined with a first light barrier plate and a second light barrier plate of another embodiment.

FIG. 3A is a schematic plan view of the portable electronic device of FIG. 1C combined with a first light barrier plate and a second light barrier plate of an embodiment. FIG. 3B is a schematic plan view of the portable electronic device of FIG. 2A combined with a first light barrier plate and a second light barrier plate of another embodiment.

With reference to FIGS. 3A and 3B, in an embodiment of the disclosure, the portable electronic device 100 further includes a first light barrier plate P1 and a second light barrier plate P2.

The first light barrier plate P1 is disposed around a first outer edge E1 of the first body 110, and the second light barrier plate P2 is disposed around a second outer edge E2 of the second body 120. With reference to FIG. 1D, the first light barrier plate P1 and the second light barrier plate P2 are tightly fitted to each other when the first body 110 and the second body 120 are closed relative to each other, so as to seal a gap G between the first body 110 and the second body 120. The light L for sterilization and disinfection (UV light) may be restricted between the first body 110 and the second body 120 by the sealing effect of the first light barrier plate P1 and the second light barrier plate P2, therefore preventing leakage of the light L for sterilization and disinfection (UV light).

With reference to FIG. 3A, in the embodiment, an end of the first light barrier plate P1 covers the gap G and is tightly fitted to an end of the second light barrier plate P2. With reference to FIG. 3B, in the embodiment, an end of the second light barrier plate P2 covers the gap G and is tightly fitted to an end of the first light barrier plate P1.

Figure 4A:
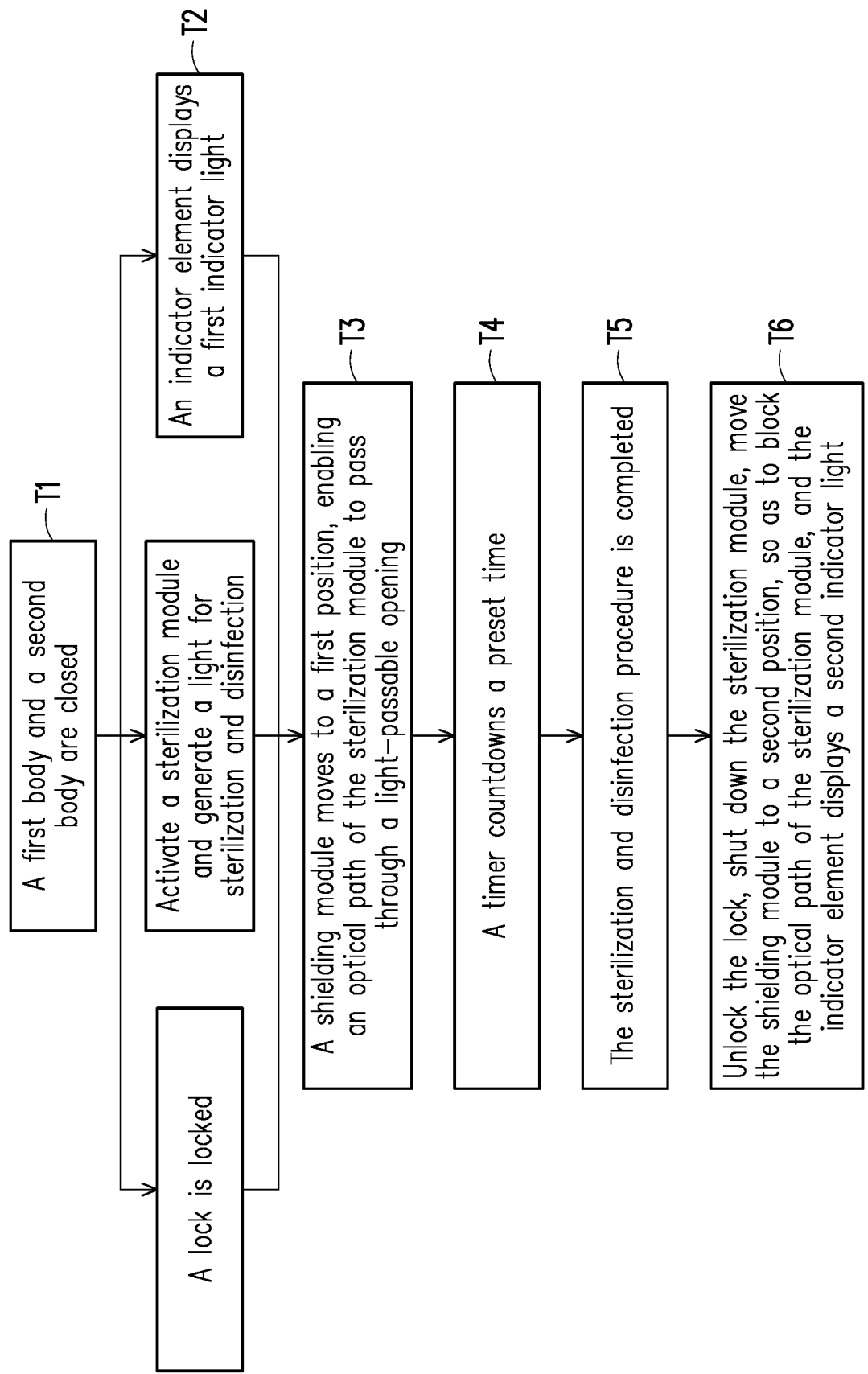
FIG. 4A is a flowchart of the portable electronic device in FIG. 1C undergoing the sterilization procedure.
Figure 4B:
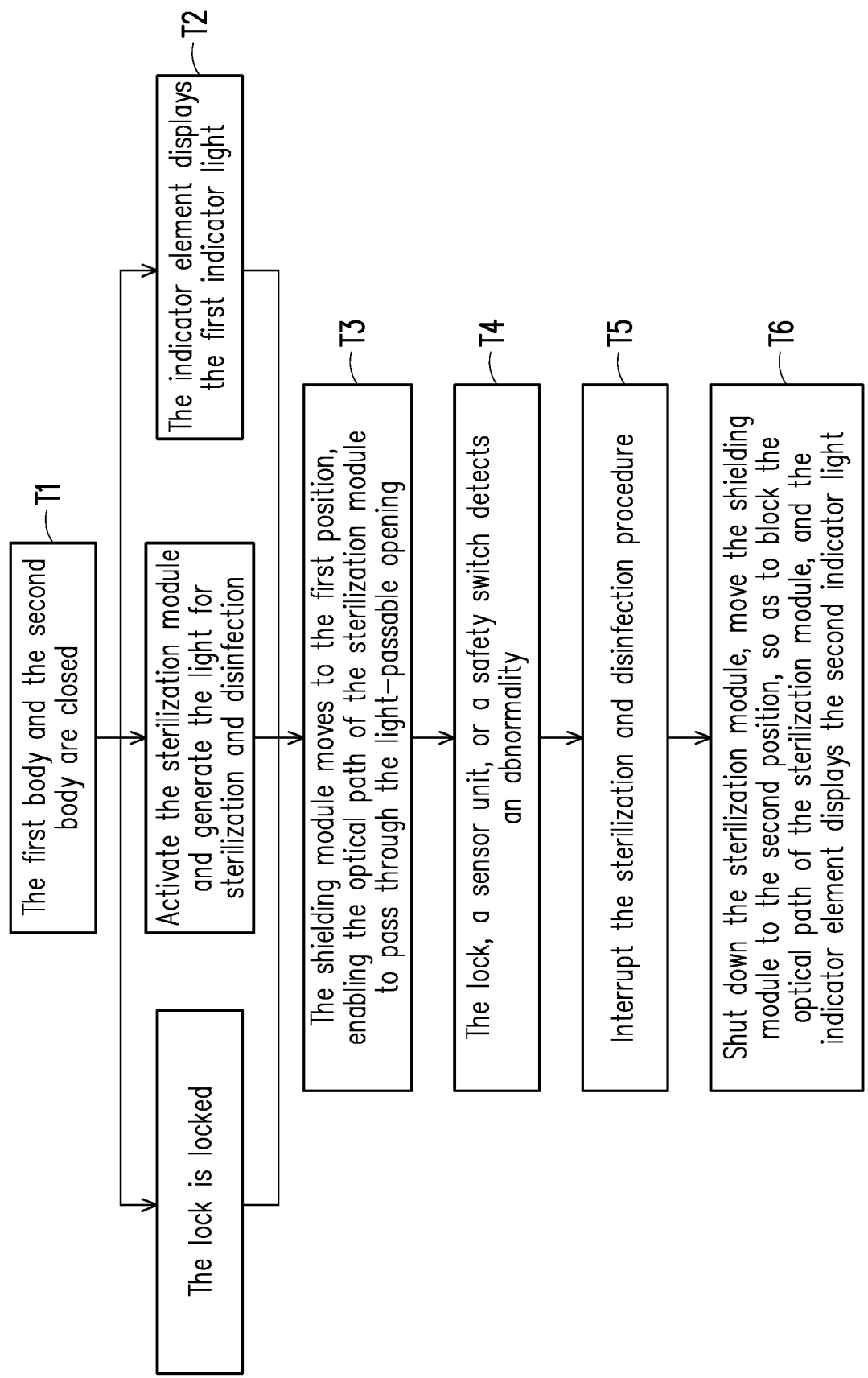
FIG. 4B is a flowchart of the portable electronic device in FIG. 1C interrupting the sterilization and disinfection procedure.

FIG. 4A is a flowchart of the portable electronic device in FIG. 1C undergoing the sterilization procedure. FIG. 4B is a flowchart of the portable electronic device in FIG. 1C interrupting the sterilization and disinfection procedure.

With reference to FIGS. 1C, 1D, 2C and 4A, an operation process of the portable electronic device undergoing the sterilization and disinfection procedure is briefly described as follows.

The control unit 140 activates the sterilization module 160 and generates the light L for sterilization and disinfection, enabling the lock 180 to be switched to a locked state, and synchronously allowing the indicator element TC to display the first indicator light (Step T2) when the first body 110 and the second body 120 of the portable electronic device 100 are closed relative to each other (Step T1). Then, the control unit 140 controls sliding of the shielding module 170 to allow the light L for sterilization and disinfection to pass through the light-passable openings H (Step T3), and the timer 190 starts to count down the preset time of the sterilization and disinfection procedure (Step T4). The control unit 140 unlocks the lock 180, that is, the lower latch 181 is unlocked from the upper latch 182 (enabling the user to unfold the first body 110 from the second body 120) after the sterilization module 160 completes the disinfection procedure (Step T5). Concurrently, the control unit 140 shuts down the sterilization module 160, so as to stop the generation of the light L for sterilization and disinfection. The control unit 140 controls sliding of the shielding module 170 to shield the sterilization module 160. The control unit 140 controls the indicator element TC to display the second indicator light (Step T6), which is configured to remind the user that the lock 180 is unlocked, the sterilization module 160 is switched to a shutdown state, the shielding module 170 shields the sterilization module 160, and the sterilization and disinfection procedure has been completed.

With reference to FIGS. 1C, 1D, 2C and 4B, an operation process of the portable electronic device interrupting the sterilization and disinfection procedure is briefing described as follows.

The control unit 140 activates the sterilization module 160 and generates the light L for sterilization and disinfection, enabling the lock 180 to be switched to the locked state, and synchronously allowing the indicator element TC to display the first indicator light (Step T2) when the first body 110 and the second body 120 of the portable electronic device 100 are closed relative to each other (Step T1). Then, the control unit 140 controls sliding of the shielding module 170 to allow the light L for sterilization and disinfection to pass through the light-passable openings H (Step T3). The control unit 140 interrupts the sterilization and disinfection procedure (Step T5) after the lock 180, the sensor unit 150 or the safety switch SW detects an abnormal condition (Step T4), such as the user actively unlocking the lock 180, the sensor unit 150 detecting collision or falling due to an external force, and the safety switch SW is displaced by an external force. Concurrently, the control unit 140 shuts down the sterilization module 160, so as to stop the generation of the light L for sterilization and disinfection. The control unit 140 drives the shielding module 170 to move to the second position N2 to block the multiple optical paths P of the sterilization module 160 (refer to FIG. 2A), so as to prevent the leakage of the light L for sterilization and disinfection. The control unit 140 controls the indicator element TC to display the second indicator light (Step T6), so as to remind the user that the lock 180 is unlocked, the sterilization module 160 is switched to the shutdown state, the shielding module 170 shields the sterilization module 160, and the sterilization and disinfection procedure has stopped.

As mentioned above, to continue the sterilization and disinfection procedure, the user has to eliminate the abnormal condition of the lock, the sensor unit and the safety switches. Then, the control unit activates the sterilization module and generates the UV light, enabling the lock to switch to the locked state, and synchronously allowing the indicator element to display the first indicator light while controlling sliding of the shielding module to allow the UV light to pass through the light-passable opening.

In summary, the portable electronic device of the disclosure includes the sterilization module, the control unit, and the sensor unit. The control unit activates the sterilization module and generates the light for sterilization and disinfection when the sensor unit detects that the first body and the second body are closed relative to each other, so as to irradiate the first inner surface of the first body and the second inner surface of the second body to achieve sterilization and disinfection. The control unit shuts down the sterilization module and uses the shielding module to block the sterilization module as a protective measure when the sensor unit detects that the first body and the second body are unfolded relative to each other, so as to prevent the leakage of the light for sterilization and disinfection from causing damage to the human body.

Furthermore, the portable electronic device automatically undergoes or shuts down the sterilization and disinfection procedure by determining whether it is in the closed state or the unfolded state, thereby replacing the existing cleaning means of manual wiping.

What is claimed is:

1. A portable electronic device, comprising:
   a first body, having a first inner surface;
   a second body, having a second inner surface;
   a hinge mechanism, connected between the second body and the first body;
   a control unit, disposed in the first body or the second body;
   a sensor unit, disposed in the first body or the second body and coupled to the control unit;
   a sterilization module, disposed in the hinge mechanism and coupled to the control unit, suitable for generating at least one light for sterilization and disinfection; and
   a shielding module, having at least one light-passable opening, disposed on the hinge mechanism and movable relative to the hinge mechanism, the shielding module is coupled to the control unit,
   wherein the control unit is suitable for activating the sterilization module and driving the shielding module to move to a first position, the at least one light-passable opening is opposite to the sterilization module, and at least one optical path of the sterilization module is suitable for irradiating the first inner surface or the second inner surface through the at least one light-passable opening when the sensor unit detects that the first body and the second body are closed relative to each other, and the control unit is suitable for shutting down the sterilization module and driving the shielding module to move to a second position to block the at least one optical path of the sterilization module when the sensor unit detects that the first body and the second body are unfolded relative to each other.

2. The portable electronic device according to claim 1, wherein the shielding module is slidably disposed on the hinge mechanism to switch between the first position and the second position.

3. The portable electronic device according to claim 1, further comprising:
a lock, coupled to the control unit and comprising a lower latch and an upper latch, wherein the lower latch is disposed at the first body and the upper latch is disposed at the second body, the control unit controls the lower latch and the upper latch to be locked to each other when the first body and the second body are closed relative to each other.

4. The portable electronic device according to claim 3, wherein the control unit shuts down the sterilization module and drives the shielding module to move to the second position when the lock is unlocked by an external force.

5. The portable electronic device according to claim 1, wherein the sterilization module comprises a plurality of ultra-violet (UV) light sources, and the light for sterilization and disinfection is a UV light.

6. The portable electronic device according to claim 1, wherein each of the lights for sterilization and disinfection is suitable for reflection and transmission between the first inner surface and the second inner surface.

7. The portable electronic device according to claim 1, further comprising:
a timer, disposed in the first body or the second body and coupled to the control unit, wherein the timer sets a preset time when the first body and the second body are closed relative to each other, and the control unit shuts down the sterilization module and drives the shielding module to move to the second position after countdown of the preset time is completed.

8. The portable electronic device according to claim 1, further comprising:
at least one safety switch, disposed on two sides of the second body away from the hinge mechanism and coupled to the control unit, wherein the control unit shuts down the sterilization module and drives the shielding module to move to the second position when the at least one safety switch is pressed by an external force.

9. The portable electronic device according to claim 3, further comprising:
an indicator element, coupled to the control unit, wherein the control unit transmits a locked signal to the indicator element and a first indicator light is displayed when the lower latch and the upper latch are locked to each other, and the control unit transmits an unlocked signal to the indicator element and a second indicator light is displayed when the lower latch and the upper latch are unlocked from each other.

10. The portable electronic device according to claim 1, further comprising:
an indicator element, coupled to the sterilization module, wherein the indicator element displays a first indicator light when the sterilization module is switched on, and the indicator element displays a second indicator light when the sterilization module is shut down.

11. The portable electronic device according to claim 1, further comprising:

an indicator element, coupled to the shielding module, wherein the indicator element displays a first indicator light when the shielding module moves to the first position, and the indicator element displays a second indicator light when the shielding module moves to the second position.

12. The portable electronic device according to claim 1, wherein the sensor unit comprises a Hall sensor and a magnetic part, the Hall sensor is disposed in the first body and coupled to the control unit, the magnetic part is disposed in the second body and is opposite to the Hall sensor, and the Hall sensor senses a change in a magnetic field of the magnetic part, so as to convert the change into an included angle between the first body and the second body.

13. The portable electronic device according to claim 1, wherein the sensor unit comprises a gravity sensor, which is disposed in the second body and coupled to the control unit.

14. The portable electronic device according to claim 5, further comprising:
a plurality of light-guiding elements, disposed in the first body, wherein each of the light-guiding elements has a light-incident portion, a guiding portion, and a light-emitting portion, each of the light-incident portions corresponds to each of the UV light sources, each of the guiding portions is distributed on the first inner surface, and each of the light-emitting portions is away from the shielding module.

15. The portable electronic device according to claim 14, wherein each of the light-guiding elements may be a light-guiding plate, a light-guiding rod, or an optical fiber.

16. The portable electronic device according to claim 1, further comprising:
a reflective layer, disposed at the first inner surface or the second inner surface corresponding to the first body and the second body.

17. The portable electronic device according to claim 1, further comprising:
a first light barrier plate and a second light barrier plate, wherein the first light barrier plate is disposed around a first outer edge of the first body, the second light barrier plate is disposed around a second outer edge of the second body, and the first light barrier plate and the second light barrier plate are tightly fitted to each other when the first body and the second body are closed relative to each other, so as to seal a gap between the first body and the second body.

18. The portable electronic device according to claim 17, wherein an end of the first light barrier plate covers the gap and is tightly fitted to an end of the second light barrier plate.

19. The portable electronic device according to claim 17, wherein an end of the second light barrier plate covers the gap and is tightly fitted to an end of the first light barrier plate.

20. A disinfecting and sterilization method, suitable for a portable electronic device having a first body, a second body, a hinge mechanism, a control unit, a sensor unit, a sterilization module and a shielding module, wherein, the hinge mechanism is connected between the second body and the first body, the control unit is disposed in the first body or the second body, the sensor unit is disposed in the first body or the second body and coupled to the control unit, the sterilization module is disposed in the hinge mechanism and coupled to the control unit, the shielding module is disposed on the hinge mechanism and movable relative to the hinge mechanism, and the shielding module is coupled to the control unit, the disinfecting and sterilization method comprising:

detecting that the first body and the second body are closed relative to each other by the sensor unit;

activating the sterilization module and generating at least one light for sterilization and disinfection by the control unit;

driving the shielding module to move to a first position by the control unit, enabling at least one optical path of the sterilization module to pass through at least one light-passable opening of the shielding module; and shutting down the sterilization module and driving the shielding module to move to a second position by the control unit, so as to block the at least one optical path of the sterilization module.

21. The disinfecting and sterilization method according to claim 20, wherein the sensor unit comprises a gravity sensor coupled to the control unit, and is configured to sense shaking of the first body or the second body, and the control unit shuts down the sterilization module and drives the shielding module to move to the second position when the sensor unit detects an abnormality.

22. The disinfecting and sterilization method according to claim 20, further comprising:

a lock, coupled to the control unit, wherein the control unit shuts down the sterilization module and drives the shielding module to move to the second position when the lock is unlocked by an external force.

23. The disinfecting and sterilization method according to claim 20, further comprising:

at least one safety switch, disposed on two sides of the second body away from the hinge mechanism and coupled to the control unit, wherein the control unit shuts down the sterilization module and drives the shielding module to move to the second position when the safety switch is pressed by an external force.

24. The disinfecting and sterilization method according to claim 20, further comprising:

a timer, disposed in the first body or the second body and coupled to the control unit, wherein the timer sets a preset time when the first body and the second body are closed relative to each other, and the control unit shuts down the sterilization module and drives the shielding module to move to the second position after countdown of the preset time is completed.

25. The disinfecting and sterilization method according to claim 22, further comprising:

an indicator element, coupled to the control unit, wherein the indicator element displays a second indicator light when the lock is unlocked by the external force.

26. The disinfecting and sterilization method according to claim 20, further comprising:

an indicator element, coupled to the sterilization module, wherein the indicator element displays a first indicator light when the sterilization module is switched on, and the indicator element displays a second indicator light when the sterilization module is shut down.

27. The disinfecting and sterilization method according to claim 20, further comprising:

an indicator element, coupled to the shielding module, wherein the indicator element displays a first indicator light when the shielding module moves to the first position, and the indicator element displays a second indicator light when the shielding module moves to the second position.

* * * * *